(12) United States Patent
Hannessen (10) Patent No.: US 8,770,385 B2
(45) Date of Patent: Jul. 8, 2014

(54) DEVICE AND METHOD FOR TRANSFERRING GOODS BETWEEN CONVEYORS

(75) Inventor: Pieter Gerrit Hannessen, Harderwijk (NL)

(73) Assignee: Nedpack Patenten B.V., Harderwijk (NL)

( * ) Notice: Subject to any disclaimer, the term of this patent is extended or adjusted under 35 U.S.C. 154(b) by 137 days.

(21) Appl. No.: 13/146,632

(22) PCT Filed: Mar. 8, 2010

(86) PCT No.: PCT/NL2010/050113
§ 371 (c)(1),
(2), (4) Date: Oct. 11, 2011

(87) PCT Pub. No.: WO2010/101463
PCT Pub. Date: Sep. 10, 2010

(65) Prior Publication Data
US 2012/0043183 A1 Feb. 23, 2012

(30) Foreign Application Priority Data
Mar. 6, 2009 (NL) .................................... 1036672

(51) Int. Cl.
*B65G 17/18* (2006.01)
*B65G 17/12* (2006.01)
*B65G 47/57* (2006.01)

(52) U.S. Cl.
CPC .............. *B65G 17/123* (2013.01); *B65G 47/57* (2013.01)

USPC ............................................ 198/607; 198/800

(58) Field of Classification Search
CPC ........................................................ B65G 17/18
USPC ........................................................ 198/475.1
See application file for complete search history.

(56) References Cited

U.S. PATENT DOCUMENTS

| 3,187,880 | A | * | 6/1965 | Frater et al. ................... 198/798 |
| 3,902,590 | A | * | 9/1975 | Raynor et al. ................ 198/798 |
| 4,846,337 | A | * | 7/1989 | Kuhlmann ................. 198/475.1 |
| 4,987,992 | A | * | 1/1991 | Pfleger ........................ 198/475.1 |
| 5,101,963 | A | * | 4/1992 | Skarlupka et al. ............ 198/800 |
| 6,321,899 | B1 | * | 11/2001 | Hannessen ................. 198/475.1 |

(Continued)

FOREIGN PATENT DOCUMENTS

| CN | 1990361 A | 7/2007 |
| DE | 10150255 A1 | 5/2003 |

(Continued)

*Primary Examiner* — Ramya Burgess
*Assistant Examiner* — Thomas Randazzo
(74) *Attorney, Agent, or Firm* — Daniel G. Stoddard; Bret E. Field; Bozicevic, Field & Francis, LLP (57) ABSTRACT

The present invention relates to a device and a method for transferring goods (6) from a first (2) to a second conveyor (4), comprising a substantially upright extending frame (8), —an endless drive arranged on the frame (8) and • drivable by a motor; at least one support member which is connected to the endless drive (24) and which is drivable in a circuit by means of the endless drive (24), —at least one product carrier (28) connected to the support member, wherein the product carrier (28) is connected to the support member for rotation about a lying shaft extending transversely of the frame, wherein the product carrier (28) is connected drivably to no more than one endless drive.

20 Claims, 7 Drawing Sheets

(56) References Cited

U.S. PATENT DOCUMENTS 6,394,260 B1  5/2002 Barth et al.
7,278,532 B2 * 10/2007 Martin .......................... 198/800
7,946,410 B2 * 5/2011 DeMong et al. .............. 198/301

FOREIGN PATENT DOCUMENTS

| | | |
|---|---|---|
| EP | 0609669 A1 | 8/1994 |
| EP | 0999152 A1 | 5/2000 |
| NL | 1023107 C2 | 10/2004 |

* cited by examiner

DEVICE AND METHOD FOR TRANSFERRING GOODS BETWEEN CONVEYORS

The present invention relates to a device and a method for transferring goods, and more particularly to a device and a method for transferring goods from a first to a second conveyor, wherein a height difference can be bridged between conveyors in substantially lying position.

The Netherlands patent NL 1 023 107 of applicant relates to a continuous vertical conveyor with curved guide tracks, which is likewise adapted to bridge a height difference between conveyors. Drawbacks of the conveyor described in this patent publication include, among others, wear of the endless drives.

An object of the present invention is to provide a device and method of the above stated type, wherein one or more drawbacks are at least partially prevented and wherein wear of the endless drives is particularly reduced.

The stated object is achieved with the device according to the invention for transferring goods from a first to a second conveyor, the device comprising:

- a substantially upright extending frame;
- an endless drive arranged on the frame and drivable by a motor;
- at least one support member which is connected to the endless drive and which is drivable in a circuit by means of the endless drive;
- at least one product carrier connected to the support member, wherein the product carrier is connected to the support member for rotation about a lying shaft extending transversely of the frame;
- wherein each product carrier is connected drivably to no more than one endless drive; and
- wherein the support member can be coupled to the frame such that the degree of freedom of the support member transversely of the plane of the frame is substantially fixed, while the support member is movable substantially freely along a predetermined path in the plane of the frame by the endless drive.

In other words, the frame has a height direction and the support member can be coupled to the frame such that the support member is movable substantially freely along a predetermined path in the height direction by the endless drive, while the position transversely of the height direction remains substantially the same. The position remains substantially the same transversely of the height direction because the movement of the support member transversely of the height direction of the frame is substantially bounded by the coupling of the support member to the frame.

Because an endless drive is applied, the predetermined path along which the support member is movable by means of the endless drive forms an endless circuit.

Because the support member can be coupled to the frame such that the degree of freedom of the support member transversely of the plane of the frame is substantially fixed, while the support member is movable substantially freely in the plane of the frame by the endless drive, the support member simultaneously provides support (rigidity) and freedom of movement to the product carrier. A single endless drive can hereby suffice, which moreover only has to function as drive. Because the function of supporting the product carrier transversely of the plane of the frame—which movement is for instance compensated by a transverse load on the endless drive in the device shown in NL 1 023 107—is absorbed according to the invention by the support member, the endless drive according to the invention is on the one hand loaded less, which already results in a significant reduction in the wear of the endless drive. A single endless drive will on the other hand suffice, whereby wear is reduced still further. If a plurality of endless drives together absorb a load—as in NL 1 023 107—differences in the stretch between the different endless drives subjected to load will after all result in uneven running, this uneven running being a significant cause of wear. Because such a coupling between endless drives is redundant according to the invention, a considerable reduction in wear of the endless drive is obtained.

A further advantage, in addition to wear of the endless drive being significantly reduced, is that the load which can be carried on the product carrier also increases considerably. This effect is obtained in that the product carrier is no longer directly coupled to an endless drive by means of a shaft and coupling elements—as in NL1 023 107—but is connected to a support member coupled to the frame. Owing to its coupling to the frame, this support member is able to absorb forces transversely of the plane of the frame. The endless drive itself only has to move the product carrier via the support member, and is itself no longer required to absorb any forces transversely of the plane of the frame. Because the support member absorbs these forces, the load-bearing capacity of the product carrier is increased, whereby heavier products can be displaced with the product carrier than has formerly been the case.

A further additional advantage is that the device is easier to adjust now that the necessity of making a plurality of endless drives run as evenly as possible is avoided because a single endless drive will suffice.

Other further advantages are that a single endless drive will suffice, whereby the device can be of more compact construction, fewer parts are necessary, and the device will moreover have a lower mass and will thereby be easier to transport and place. Because the number of parts has been reduced, reliability is moreover further increased.

For the sake of completeness it is noted that the wording 'that the degree of freedom . . . is substantially fixed' must be understood to mean a restraining which significantly reduces movement in this direction relative to the frame but which does not necessarily completely prevent absolute movement. It is for instance thus possible to envisage the frame itself deforming to some extent when a large load is being carried by the product carrier, while the frame does however maintain the situation where the degree of freedom is substantially fixed according to the teaching of the present invention.

The degree of freedom of translations of the movement in the plane of the frame are linked to the endless drive. The degree of freedom of the rotation of the lying shaft which extends relative to the plane of the frame and with which the product carrier is arranged on the support member is linked to guide means. These guide means are adapted to hold the product carrier substantially in a horizontal position.

The product carrier is connected drivably to no more than one endless drive. This endless drive has only a driving function, while the support member connected to the endless drive has a supporting function. Owing to this support member a second endless drive—as in NL1 023 107—is redundant.

According to a preferred embodiment, a single endless drive is applied, although it is also possible to envisage a plurality of endless drives movable independently of each other being applied. A single endless drive can suffice because the endless drive functions only for the purpose of driving the support member but need not provide any support in transverse direction. The skilled person will appreciate that a device according to the present invention can comprise a plurality of—independently operating—endless drives, for instance one on both sides of the frame. These are endless drives operating independently of each other which can for instance each be applied for a direction of movement of their own, wherein it is also possible to envisage that the speed of the movement of the two drives differs.

It is expressly noted that the invention relates only to embodiments wherein—if a plurality of endless drives are applied—these endless drives are independent of each other. Independent means that a single product carrier is in drivable mechanical connection with no more than one endless drive and the endless drives are not mutually coupled.

It is of course possible to envisage a plurality of product carriers being drivably connected to one common endless drive. These product carriers, distributed at some mutual distance over the endless circuit, increase the transfer capacity proportionally to the number of product carriers.

According to a further preferred embodiment, the endless drive is tensioned between at least an upper running wheel and a lower running wheel, wherein at least one of the two running wheels is drivable by the motor. Because the running wheels are placed one above the other, the endless drive tensioned over these running wheels provides a driving which extends in height direction over the substantially upright extending frame. The device is hereby suitable for transferring goods between conveyors between which there is a height difference.

According to a further preferred embodiment, the support member can be coupled to one or more running wheels of the endless drive such that the degree of freedom of the support member transversely of the plane of the frame is substantially fixed, while the support member is substantially freely movable in the plane of the frame by the endless drive. Because the support member can be coupled to one or more running wheels, these running wheels function as support while the support member runs through a bend. Due to its coupling to the running wheel the support member can move only to a very small extent transversely of the plane of the frame, whereby this degree of freedom is substantially fixed. Although it is possible to envisage the support member running over a plate-like surface, such as a front plate of the frame, a coupling with the running wheel has the further advantage that a relative standstill can take place between the support member and the running wheel. This relative standstill means that the running wheel co-displaces with the movement of the support member, whereby the running wheel and support member are substantially at a standstill relative to each other. Wear between the two parts is hereby reduced to a minimum.

Because the support member according to this preferred embodiment can also be coupled to one or more running wheels of the endless drive as well as to the frame, the support member can be coupled substantially over a full circuit to a support-providing part, respectively the frame or a running wheel, whereby the degree of freedom of the support member transversely of the plane of the frame can be ensured during a full movement through the endless circuit.

Although it is possible to envisage the frame enclosing the support member, in a preferred embodiment the support member at least partially encloses the frame and/or the running wheel in order to thus obtain the coupling between the support member and/or the running wheel. Because the support member itself encloses the support-providing part formed by the frame or the running wheels, it is possible to couple the support member to the running wheel. A coupling is hereby ensured over a movement through a full circuit.

According to yet another preferred embodiment, the frame comprises close to the running wheels a guide wall for guiding thereover at least the side of the support member remote from the running wheel. This side of the support member remote from the running wheel, i.e. the side of the support member which follows the outer bend, can be guided over a guide wall so that it is thereby coupled to the frame. In addition to a coupling to the running wheel, in this way a coupling to the frame—on the outer side of a bend—is also ensured during passage through the bend.

According to yet another preferred embodiment, the support member is provided with wheels with a friction coefficient below 0.1. Although it is possible to envisage sliding contact by means of slide shoes between the support member and the support-providing parts, respectively frame or running wheels, when use is made of a wear-resistant material with a low friction coefficient, such as for instance nylon or a homogeneous polyurethane elastomer of high quality or polyamide, wheels are preferably applied. Because these wheels can roll, the frictional resistance is further reduced. During passage through a bend, in addition to a rolling movement of the wheels a guiding movement of the wheels will also take place, in which case a low friction coefficient of less than 0.1 is desirable.

In addition to slide shoes and wheels, it is also possible to envisage ball races being applied. A ball race comprises a ball shell filled with one large ball supported by a large number of small balls. The advantage of ball races is their high load-bearing capacity.

According to another further preferred embodiment, the wheels of the support member are manufactured from nylon.

According to another further preferred embodiment, the device further comprises guide means adapted to hold the product carrier substantially in horizontal position, the guide means comprising at least four guide wheels which come into contact pairwise with a guide track.

According to a further preferred embodiment, the device comprises a plurality of support members, distributed at some distance from each other over the endless drive, having in each case a product carrier coupled thereto. An increase in the capacity of the device can be obtained by applying a plurality of product carriers preferably distributed over roughly equal distances.

According to a further embodiment, the first and/or the second conveyor is a rope conveyor or roller conveyor, and the product carrier comprises fingers, arranged roughly parallel and at some distance from each other, for dropping between the ropes of the rope conveyor or between the rollers of the roller conveyor. Product transitions are hereby prevented, this being advantageous in the case of unstable products or products with variable dimensions. The product carrier supports the product arranged on the product carrier at all times, whereby it is possible to avoid the product having to be gripped with for instance clamps or suction cups.

According to yet another preferred embodiment, the distance between the ropes of the rope conveyor and/or between the rollers of the roller conveyor is at least greater than the width of the fingers, so that these fingers can be moved in reliable manner between the ropes and/or rollers.

According to another further preferred embodiment, the endless drive comprises a rope, chain, belt or cable.

The present invention further relates to a method for transferring goods from a first to a second conveyor, comprising the steps of: moving a support member with product carrier connected thereto upward along a substantially upright extending frame by means of a motor-driven endless drive until the product carrier is at a higher position than the first conveyor, wherein the product carrier takes a product from the conveyor, and wherein the product carrier is connected drivably to no more than one endless drive, moving the product carrier downward to a position lower than the second conveyor, wherein the product remains on the second conveyor; and substantially fixing a degree of freedom of the support member through the coupling of the support member to the frame, wherein this substantially fixed degree of freedom is oriented transversely of the plane of the frame, while the support member can be moved substantially freely in the plane of the frame by the endless drive.

The present invention further relates to a method wherein a device as described in this document is applied.

Preferred embodiments of the present invention are further elucidated in the following description with reference to the drawing, in which.

Figure 1:
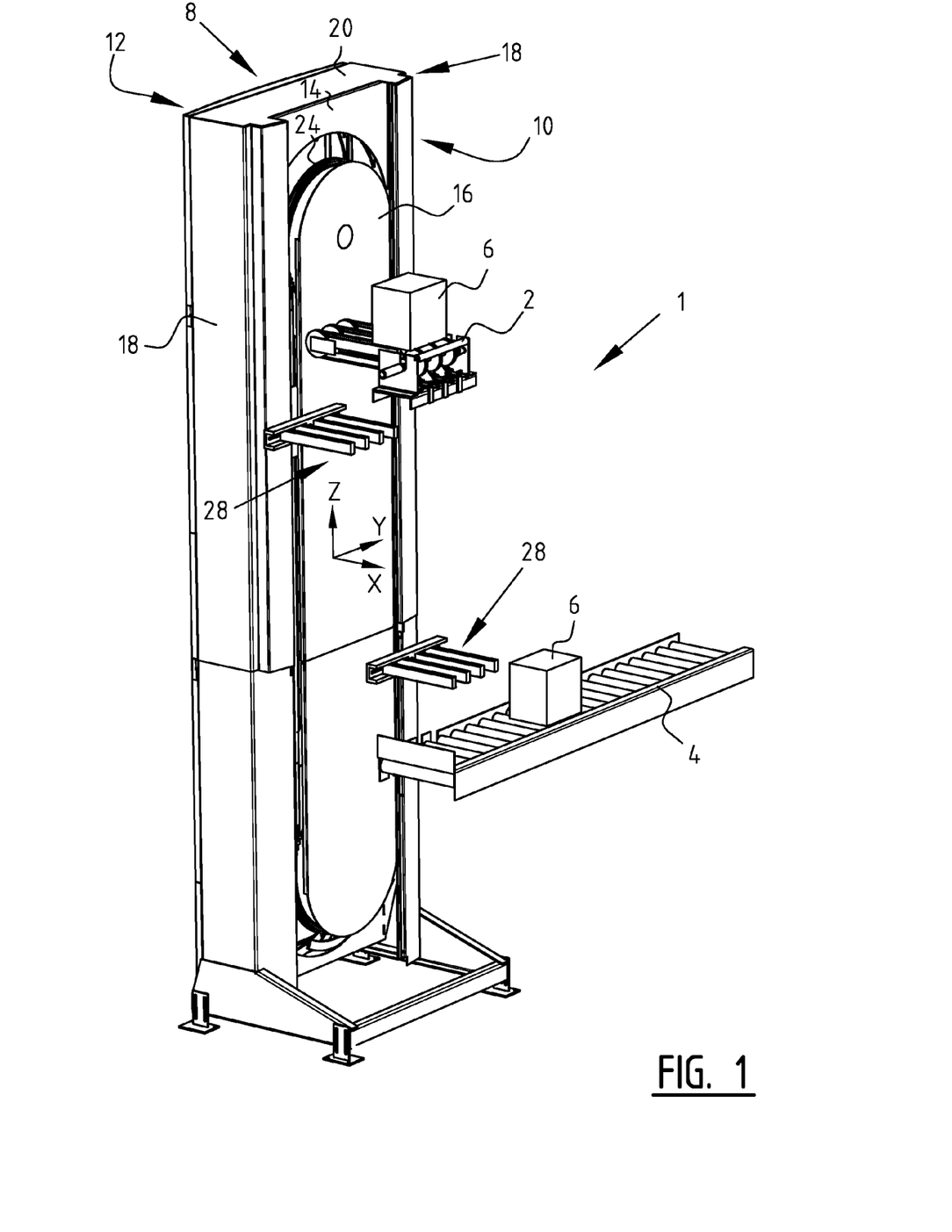
FIG. 1 is a perspective front view of a transferring device according to the present invention.
Figure 2:
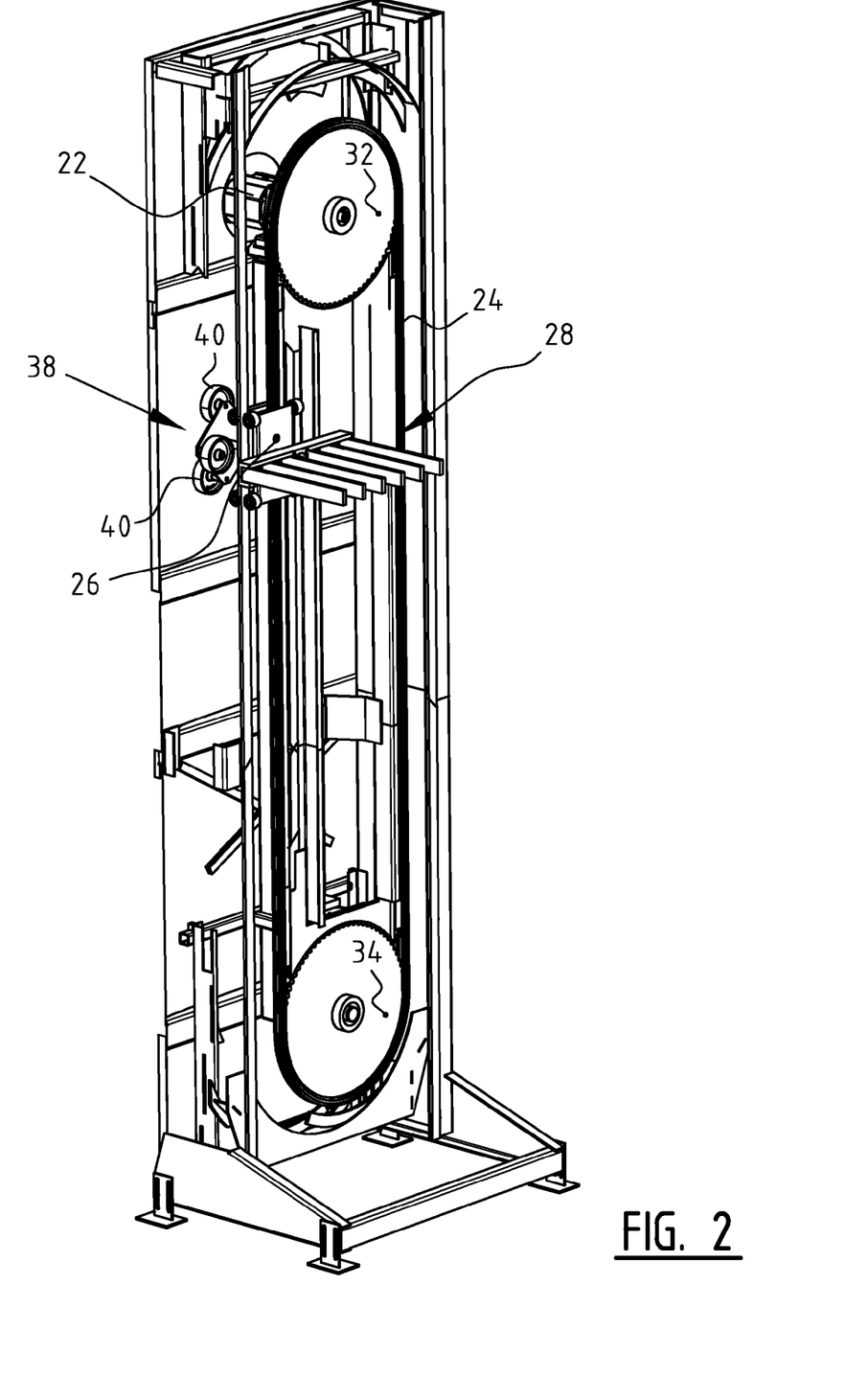
FIG. 2 is a cut-away perspective front view of the transferring device shown in FIG. 1.

The device 1 shown in FIG. 1 for transferring goods, such as products 6, from a first conveyor 2 to a second conveyor 4 comprises a substantially upright extending frame 8. This frame has a front side 10 comprising a guide wall 14 and a front plate 16. Frame 8 further has a rear side 12, side walls 18 and a top wall 20. Arranged in frame 8 is an endless drive 24, in the shown embodiment a chain, which is adapted to move one or more product carriers 28 along frame 8, wherein a height difference can be bridged between first conveyor 2 and second conveyor 4. In the shown embodiment first conveyor 2 is a rope conveyor and second conveyor 4 is a roller conveyor. Product carrier 28 is rotatable about a lying shaft which extends transversely of the frame (in the X-direction) and which is connected to support member 26 (FIG. 2). Support member 26 can be coupled to frame 8 such that the degree of freedom of support member 26 transversely of the plane of frame 8 is substantially fixed. In FIG. 1 this direction is indicated with X. Support member 26 can be moved substantially freely in the plane of frame 8 with endless drive 24, this plane being described by directions Y and Z.

Figure 3:
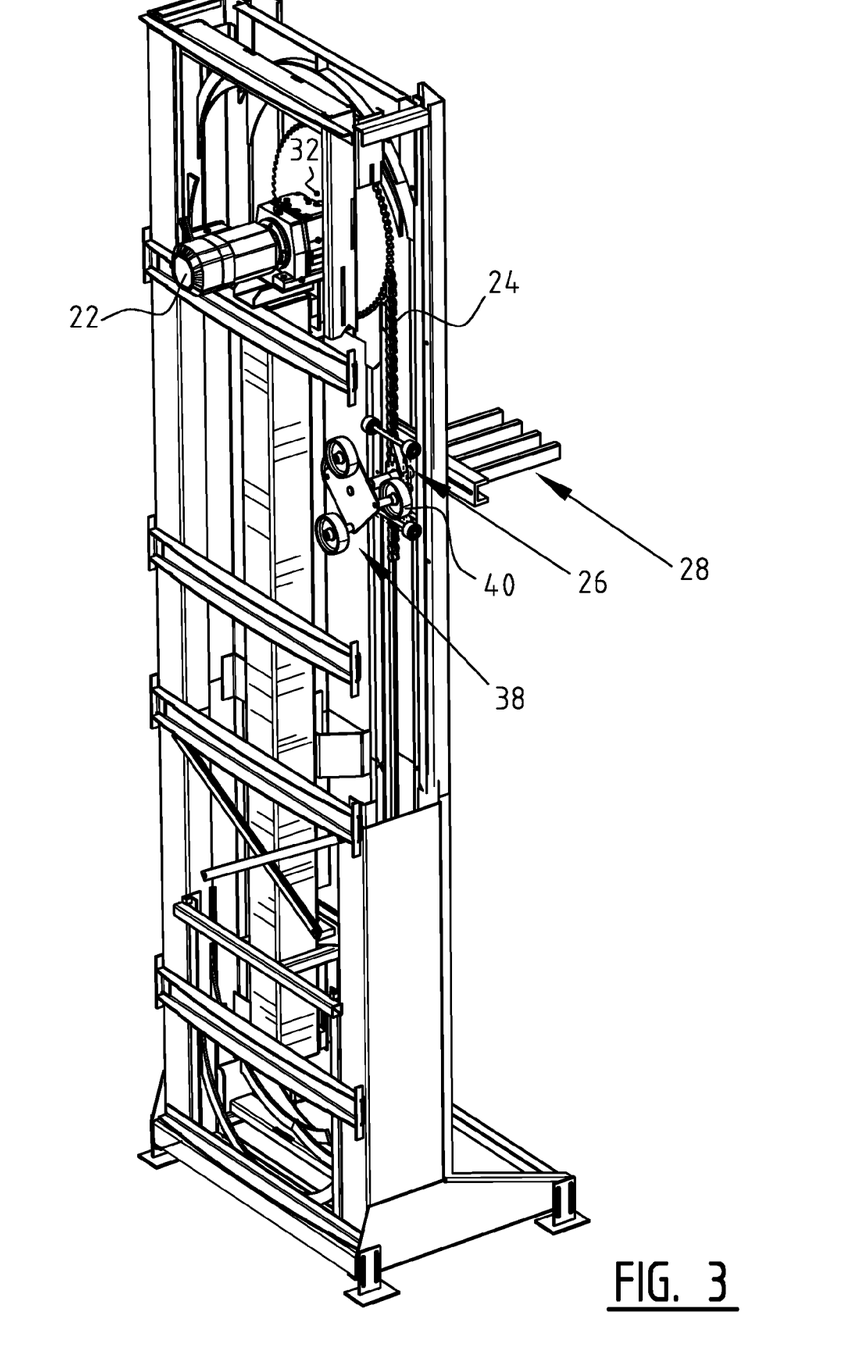
FIG. 3 is a cut-away perspective rear view of the device shown in FIG. 1.

FIG. 2 shows how endless drive 24 is tensioned and drivable between an upper running wheel 32 and a lower running wheel 34. In the shown embodiment the upper running wheel 32 can be driven by motor 22 so that product carrier 28 can be moved up and downward along frame 28. Support member 26 is further coupled to guide means 38 comprising guide wheels 40 and associated guide tracks 42. These guide means 38 are adapted to hold product carrier 28 substantially in a horizontal position and brings this about by causing a pair of the four guide wheels 40 at a time to come into contact with guide tracks 42 mounted on the frame (FIGS. 2 and 3).

Figure 4:
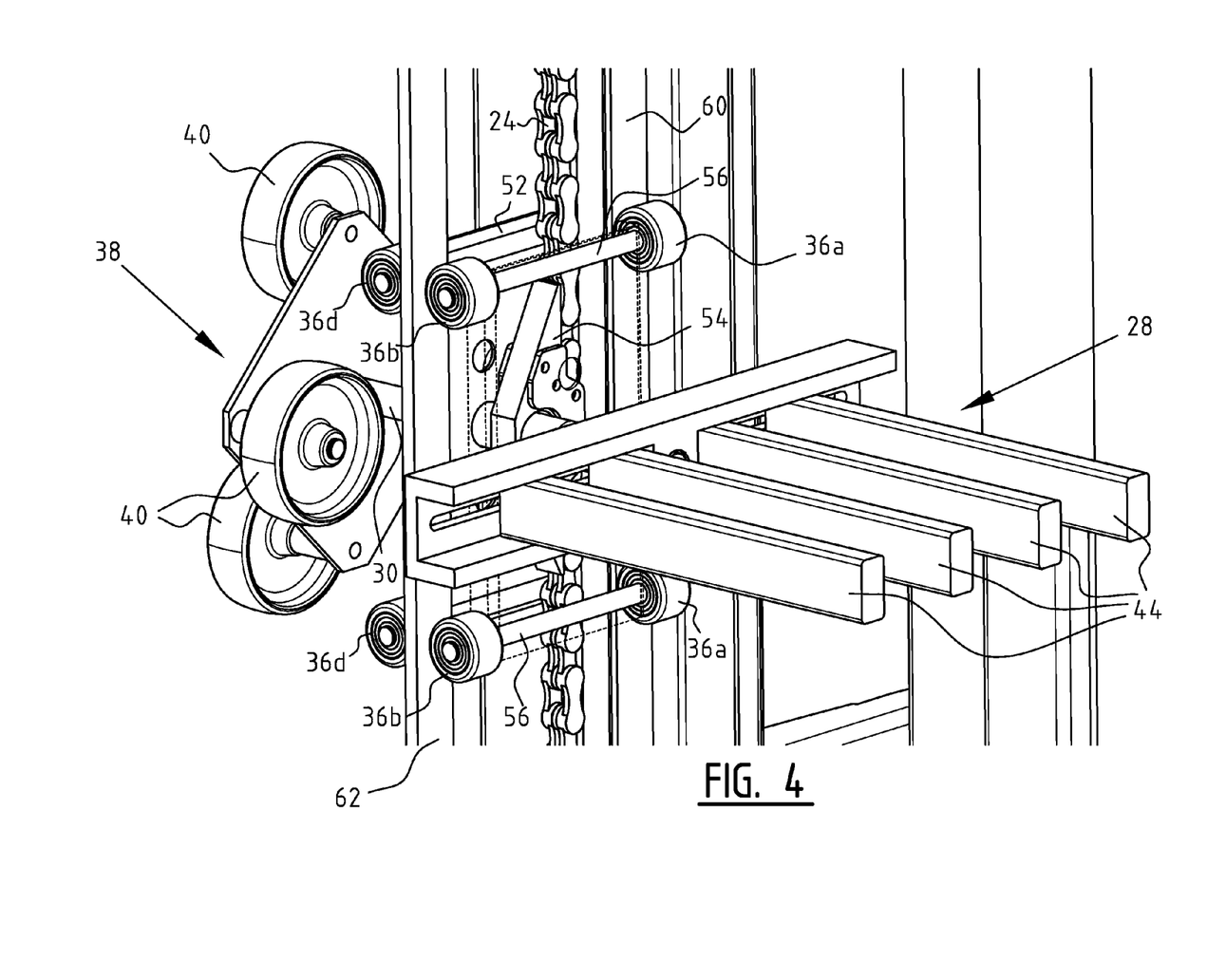
FIG. 4 is a detailed perspective front view of a product carrier with associated support member according to the present invention.
Figure 5:
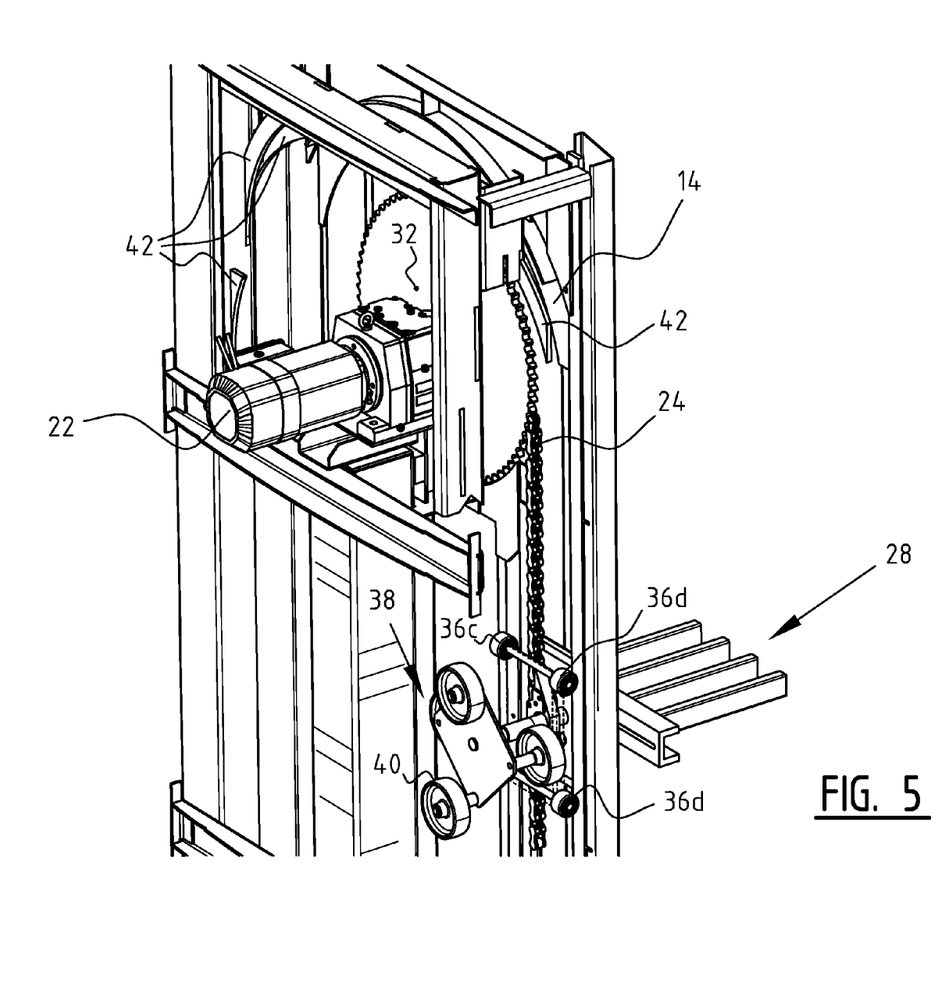
FIG. 5 is a detailed perspective rear view of the device shown in FIG. 3.

In the detailed view of FIG. 4 support member 26 is drawn partially cut-away through the omission of front plate 50 of support member 26. FIG. 4 hereby shows how support member 26 is mounted on endless drive 24 by means of a coupling element 54. Support member 26 is provided with wheels 36a-d which are mounted on support member 26 by means of shafts 56. Product carrier 28 is attached to the support member by means of a shaft 30 and can be rotated about this shaft 30 such that product carrier 28 is held in a substantially horizontal position by means of guide means 38. Guide means 38 comprise the guide wheels 40 shown in FIG. 4, which can engage on guide tracks 42 (see for instance FIG. 5).

Support member 26 comprises a total of eight wheels 36a-d, respectively wheels 36a situated on the inner radius of the endless circuit and on the front side, wheels 36b likewise situated on the front side but then on the outer radius of the endless circuit, wheels 36c which are arranged on the inner radius on the rear side and wheels 36d which are situated on the rear side and follow the outer radius of the endless circuit. Wheels 36a and 36c together enclose a strip 60 of frame 8, while wheels 36b and 36d enclose a similar strip 62 of frame 8 in order to thus couple support member 26 to frame 8.

Product carrier 28 comprises fingers 44 which have dimensions such that these fingers 44 of product carrier 28 can drop between ropes 46 of rope conveyor 2 and rollers 48 of roller conveyor 4.

Figure 6:
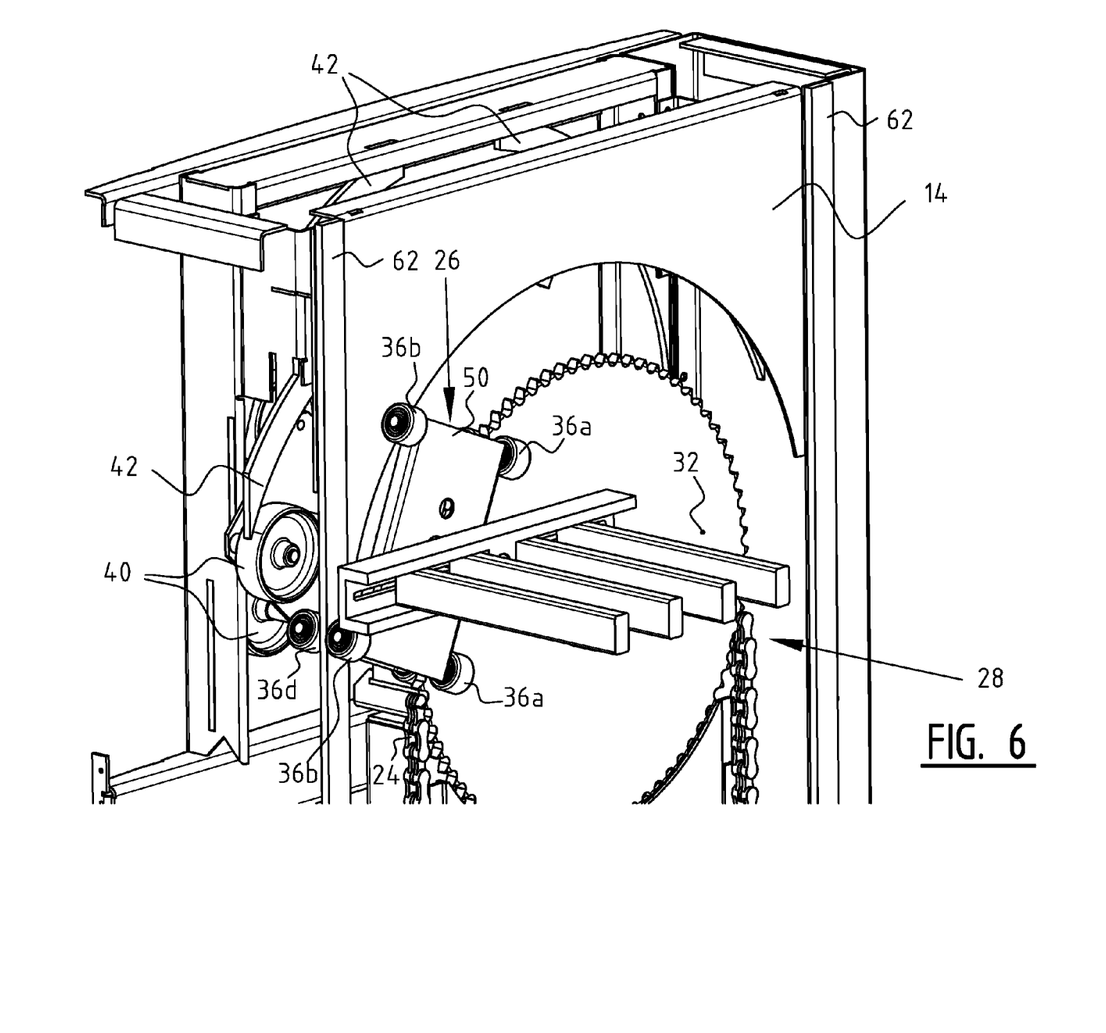
FIG. 6 is a detailed perspective front view, wherein the support member passes through a bend.
Figure 7:
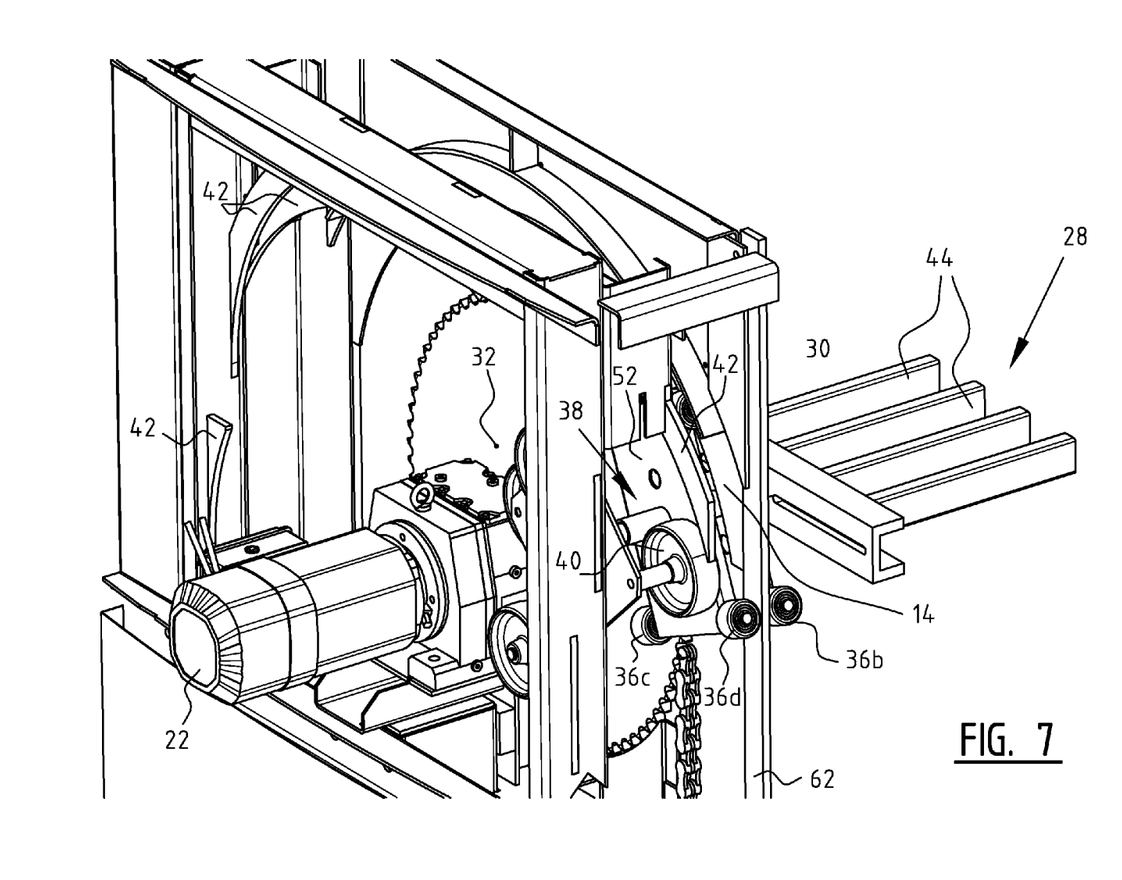
FIG. 7 is a detailed perspective rear view of the situation shown in FIG. 6.

In the position of support member 26 shown in FIG. 6 it can be seen that, as it passes through a bend with wheels 36a and 36c, it encloses a running wheel 32 of endless drive 24 while the wheels 36b and 36d situated on the outer radius of the path transpose from an enclosure of strip 62 to an enclosure of guide wall 14 of frame 8. Guide wheels 40 of guide means 38 run against guide tracks 42, whereby product carrier 28 is held substantially horizontally while support member 26 passes through the bend of the endless circuit. Wheels 36a and 36c displace at substantially the same speed as running wheel 32, whereby there is a small relative difference in speed. Wheels 36a and 36c can substantially stand still, while wheels 36b and 36d enclose guide wall 14 and move therealong. In addition to a rolling movement, wheels 36b and 36d here also make a slight sliding movement, for which purpose the wheels are embodied with a material with a low friction coefficient, such as for instance nylon. The cut-away rear view shown in FIG. 7 clearly shows how wheels 36c enclose running wheel 32 and how wheels 36d of strip 62 transpose to guide wall 14.

Although they show preferred embodiments of the invention, the above described embodiments are intended merely to illustrate the present invention and not in any way to limit the specification of the invention. The scope of the invention is therefore defined solely by the following claims.

The invention claimed is:

1. A device for transferring goods from a first to a second conveyor, the device comprising:
   a substantially upright extending frame;
   an endless drive arranged on the frame and drivable by a motor;
   at least one support member which is connected to the endless drive and which is drivable in a circuit by means of the endless drive; and
   at least one product carrier connected to the support member, wherein the product carrier is connected to the support member for rotation about a lying shaft extending transversely of the frame;
   wherein the product carrier is connected drivably to no more than one endless drive;
   wherein the support member comprises a first wheel configured to roll along a first side of the frame, and a second wheel configured to roll along a second side of the frame which is opposite the first side, and wherein the support member at least partially encloses the frame between the first wheel and the second wheel; and
   wherein the support member at least partially encloses the frame, a running wheel of the endless drive, or a combination thereof, in order to thus obtain the coupling between the support member and the frame, the running wheel, or a combination thereof such that the degree of freedom of the support member transversely of the plane of the frame is substantially fixed, while the support member is movable substantially freely along a predetermined path in the plane of the frame by the endless drive.

2. The device as claimed in claim 1, wherein a single endless drive is applied.

3. The device as claimed in claim 1, wherein a plurality of endless drives movable independently of each other are applied.

4. The device as claimed in claim 3, wherein at least two product carriers are drivably connected to one common endless drive.

5. The device as claimed in claim 1, wherein the endless drive is tensioned between at least an upper running wheel and a lower running wheel, wherein at least one of the two running wheels is drivable by the motor.

6. The device as claimed in claim 5, wherein the support member can be coupled to one or more running wheels of the endless drive such that the degree of freedom of the support member transversely of the plane of the frame is substantially fixed, while the support member is substantially freely movable in the plane of the frame by the endless drive.

7. The device as claimed in claim 1, wherein the frame comprises close to the running wheels a guide wall for guiding thereover at least the side of the support member remote from the running wheel.

8. The device as claimed in claim 1, wherein the support member is provided with wheels with a friction coefficient below 0.1.

9. The device as claimed in claim 8, wherein the wheels of the support member are manufactured from nylon.

10. The device as claimed in claim 1, further comprising guide means adapted to hold the product carrier substantially in a horizontal position, the guide means comprising at least four guide wheels which come into contact pairwise with a guide track.

11. The device as claimed in claim 1, comprising a plurality of support members with product carrier coupled thereto and distributed at some distance from each other over the endless drive.

12. The device as claimed in claim 1, wherein the first conveyor is a rope conveyor or roller conveyor, and wherein the product carrier comprises fingers, arranged roughly parallel and at some distance from each other, for dropping between the ropes of the rope conveyor or between the rollers of the roller conveyor.

13. The device as claimed in claim 12, wherein the distance between the ropes of the rope conveyor and/or between the rollers of the roller conveyor is at least greater than the width of the fingers.

14. The device as claimed in claim 1, wherein the endless drive comprises a rope, chain, belt or cable.

15. The device as claimed in claim 1, wherein the second conveyor is a rope conveyor or roller conveyor, and wherein the product carrier comprises fingers, arranged roughly parallel and at some distance from each other, for dropping between the ropes of the rope conveyor or between the rollers of the roller conveyor.

16. The device as claimed in claim 1, wherein the first and the second conveyors are rope conveyors or roller conveyors, and wherein the product carrier comprises fingers, arranged roughly parallel and at some distance from each other, for dropping between the ropes of the rope conveyors or between the rollers of the roller conveyors.

17. The device as claimed in claim 1, wherein the support member comprises a first wheel on a first side of a portion of the frame and a second wheel on a second side of the portion of the frame opposite the first side.

18. The device as claimed in claim 17, wherein the support member further comprises a front plate on the first side of a portion of the frame and a rear plate on the second side of a portion of the frame, and wherein the first wheel is mounted on the front plate, and the second wheel is mounted on the rear plate.

19. A method for transferring goods from a first to a second conveyor, the method comprising the steps of:
  moving a support member with product carrier connected thereto upward along a substantially upright extending frame by means of a motor-driven endless drive until the product carrier is at a higher position than the first conveyor, wherein the product carrier takes a product from the first conveyor, wherein the product carrier is connected drivably to no more than one endless drive, wherein the support member comprises a first wheel configured to roll along a first side of the frame, and a second wheel configured to roll along a second side of the frame which is opposite the first side, wherein the support member at least partially encloses the frame between the first wheel and the second wheel, and wherein the support member at least partially encloses the frame, a running wheel of the endless drive, or a combination thereof, in order to thus obtain the coupling between the support member and the frame, the running wheel, or a combination thereof;
  moving the product carrier downward to a position lower than the second conveyor, wherein the product remains on the second conveyor; and
  substantially fixing a degree of freedom of the support member through the coupling of the support member to the frame, wherein this substantially fixed degree of freedom is oriented transversely of the plane of the frame, while the support member can be moved substantially freely in the plane of the frame by the endless drive.

20. The method as claimed in claim 19, wherein a device for transferring goods from a first to a second conveyor is applied, wherein the device comprises:
  a substantially upright extending frame;
  an endless drive arranged on the frame and drivable by a motor;
  at least one support member which is connected to the endless drive and which is drivable in a circuit by means of the endless drive; and
  at least one product carrier connected to the support member, wherein the product carrier is connected to the support member for rotation about a lying shaft extending transversely of the frame;
  wherein the product carrier is connected drivably to no more than one endless drive; and
  wherein the support member at least partially encloses the frame, a running wheel of the endless drive, or a combination thereof, in order to thus obtain the coupling between the support member and the frame, the running wheel, or a combination thereof such that the degree of freedom of the support member transversely of the plane of the frame is substantially fixed, while the support member is movable substantially freely along a predetermined path in the plane of the frame by the endless drive.

\* \* \* \* \*